United States Patent [19]

Steer et al.

[11] 4,372,308

[45] Feb. 8, 1983

[54] OSTOMY BAG INCLUDING FILTER MEANS

[75] Inventors: Peter L. Steer; John V. Edwards, both of East Grinstead, England

[73] Assignee: Kingsdown Medical Consultants Ltd., London, England

[21] Appl. No.: 923,127

[22] Filed: Jul. 10, 1978

[51] Int. Cl.³ .............................................. A61F 5/44
[52] U.S. Cl. ..................................................... 128/283
[58] Field of Search ............... 128/283, 293, 294–295, 128/275; 55/387

[56] References Cited

U.S. PATENT DOCUMENTS

| | | |
|---|---|---|
| 1,656,328 | 1/1926 | Le Cras . |
| 1,794,940 | 3/1931 | Zimmermann ...................... 55/387 |
| 2,054,535 | 9/1936 | Diack .................................. 128/283 |
| 2,327,514 | 8/1943 | Fenwick ............................. 128/283 |
| 2,496,175 | 1/1950 | Perry .................................. 128/283 |
| 2,542,233 | 2/1951 | Carroll ............................... 128/283 |
| 2,544,579 | 3/1951 | Ardner ............................... 128/283 |
| 2,555,086 | 5/1951 | Guinn ................................. 128/283 |
| 2,652,055 | 9/1953 | Baron ................................. 128/283 |
| 2,655,153 | 10/1953 | Klotz ................................. 128/283 |
| 2,667,167 | 1/1954 | Raiche ............................... 128/283 |
| 2,669,235 | 2/1954 | Burton ............................... 128/283 |
| 2,679,248 | 5/1954 | Fullaway ........................... 128/283 |
| 2,688,327 | 9/1954 | Berg .................................. 128/283 |
| 3,039,464 | 6/1962 | Galindo ............................. 128/283 |
| 3,055,368 | 9/1962 | Baxter ............................... 128/283 |
| 3,089,493 | 5/1963 | Galindo ............................. 128/283 |
| 3,216,420 | 11/1963 | Smith et al. ..................... 128/283 |
| 3,439,677 | 4/1969 | Bonfils .............................. 128/283 |
| 3,759,260 | 9/1973 | Nolan et al. ...................... 128/283 |
| 3,804,091 | 4/1974 | Nolan et al. ...................... 128/283 |
| 3,865,109 | 2/1975 | Elmore et al. ................... 128/283 |
| 3,952,727 | 4/1976 | Nolan ................................ 128/283 |

FOREIGN PATENT DOCUMENTS

| | | |
|---|---|---|
| 631987 | 12/1961 | Canada . |
| 2310739 | 12/1976 | France . |
| 576181 | 3/1922 | United Kingdom . |
| 217480 | 6/1924 | United Kingdom . |
| 785562 | 10/1932 | United Kingdom . |
| 555852 | 9/1941 | United Kingdom . |
| 1212904 | 11/1970 | United Kingdom . |
| 1301101 | 12/1972 | United Kingdom . |
| 1363644 | 8/1974 | United Kingdom . |
| 1416594 | 2/1975 | United Kingdom . |
| 1541565 | 3/1979 | United Kingdom . |

Primary Examiner—C. Fred Rosenbaum
Attorney, Agent, or Firm—Lawrence S. Levinson; Stephen B. Davis

[57] ABSTRACT

An ostomy bag formed by welding two sheets of plastic material substantially around their periphery. The rear wall of the bag includes means to attach the bag to the user and the peripheral seal is interrupted at one or more places along the top edge of the bag. Filtering material such as carbon cloth or a housing containing filtering material can be welded in place between the front and rear walls of the bag at the opening in the peripheral seal. In one preferred embodiment, the filter element comprises a mounting block sealed into the top peripheral edge and a cartridge containing filtering material which is inserted in the mounting block.

6 Claims, 4 Drawing Figures

OSTOMY BAG INCLUDING FILTER MEANS

BACKGROUND OF THE INVENTION

Most ostomates employ some type of bag or pouch system to collect bodily wastes discharged from their surgically created stoma. Today, such bags are generally formed of light weight, odor proof, flexible polymeric materials and the collection systems are designed to be inconspicuous and permit the ostomate to engage in normal physical activity. However, many ostomates, particularly immediately following surgery, have fears concerning their ability to resume a "normal" life. These fears center around worries that the collection system will leak or that odor will escape and that the system will be noticeable even through their outer clothing. Part of these problems are due to the discharge of flatus into the bag which can cause an embarrassing distension of the bag.

In order to overcome the problem of gas build up within the collecting system, it had been suggested to provide a vent opening either in the bag or in the portion of the device which attaches to the body. For example, Cras in U.S. Pat. No. 1,656,328 provides a relief orifice in the pouch, Franklin in British Pat. No. 217,480 and Bradley et al. in British Pat. No. 555,852 provide ventilation holes, Oliver in British Pat. No. 576,181 provides a valve in the collection container, Perry in U.S. Pat. No. 2,496,175 provides a vent opening, Carroll in U.S. Pat. No. 2,542,233 disclose a colostomy guard including vent openings, Baron in U.S. Pat. No. 2,652,055 disclose a colostomy device having vent openings in the disk which surrounds the stoma, Klotz in U.S. Pat. No. 2,655,153 disclose a pouch having a vent opening, Fullaway in U.S. Pat. No. 2,679,248 discloses a colostomy shield having vent openings, Galindo in U.S. Pat. Nos. 3,039,464 and 3,089,493 and Smith et al. in U.S. Pat. No. 3,216,420 disclose bags which include gas relief valves, Sorensen in British Pat. No. 785,562 and Hansen in Canadian Pat. No. 631,987 disclose disposable bags having an adhesive disk which is used to seal a puncture made in the bag wall to relieve gas pressure, Baxter in U.S. Pat. No. 3,055,368 discloses a disposable pouch having an opening in the top edge for the escape of gas, Elmore et al. in U.S. Pat. No. 3,865,109 disclose a pouch having vent means in the outer wall, and Richardson in British Pat. No. 1,212,904 disclose vent means in the clamping ring whereby gas can be forced out of the bag. Other devices for the release of excess gas are disclosed by Diack in U.S. Pat. No. 2,054,535, Raiche in U.S. Pat. No. 2,667,167 and Caldwell in British Pat. No. 1,363,644.

Devices have also been proposed to deodorize or filter the gas before it is vented from the bag. For example, Fenwick in U.S. Pat. No. 2,327,514 includes a deodorant within the colostomy protector, Ardner in U.S. Pat. No. 2,544,579 and Guinn in U.S. Pat. No. 2,555,086 include a filtering or deodorizing element over the vent opening, Burton in U.S. Pat. No. 2,669,235 and Berg in U.S. Pat. No. 2,688,327 also disclose deodorizing the gas prior to venting, Bonfils in U.S. Pat. No. 3,439,677 discloses a bag having a vent opening in the outer wall covered by filter material, Nolan et al. in U.S. Pat. Nos. 3,759,260 and 3,804,091 disclose a pouch having an activated carbon fiber filter over the vent opening, Nolan in U.S. Pat. No. 3,952,727 disclose a particular type of filter arrangement, and British Pat. No. 1,416,594 and French Pat. No. 2,310,739 also disclose filtering the gas prior to venting.

SUMMARY OF THE INVENTION

This invention relates to an ostomy bag having means to filter gas trapped within the bag prior to venting. The term ostomy bag is meant to include an ileostomy bag, a colostomy bag, a cecostomy bag, or a like bag for use by a patient who has been subjected to surgery to produce an artificial orifice from the body, from which body wastes are expelled.

The ostomy bag is formed by a front wall and a back wall both of plastics material which are sealed together around their periphery except at one or more regions each of which defines an orifice for the escape of gas. The orifices are located at the top edge of the bag when it is attached to the body of the user. A filtering element is located in juxtaposition with the orifice so that gases escaping through the orifice will be filtered.

In the simplest embodiment of this invention, the filtering element is woven carbon cloth consisting principally of carbon in an activated state which is welded into place between the front and rear walls of the bag at the area of the unsealed top edge. The welding is carried out in such a manner that the walls are not connected where there is filter material, although they are connected around the rest of the periphery of the bag.

As an alternative embodiment, a housing containing filtering material can be welded into place between the front and rear bag walls in the area of the unsealed top edge. The housing is preferably a thin rectangular block of plastics material with the bag walls being welded to the long sides of the housing.

As a further modification, the housing can have a series of holes into which a cartridge containing filtering material can be inserted. The cartridge has hollow pins which snugly fit into the holes and an open top through which the filtered gas is vented.

DETAILED DESCRIPTION OF THE INVENTION

Figure 1:
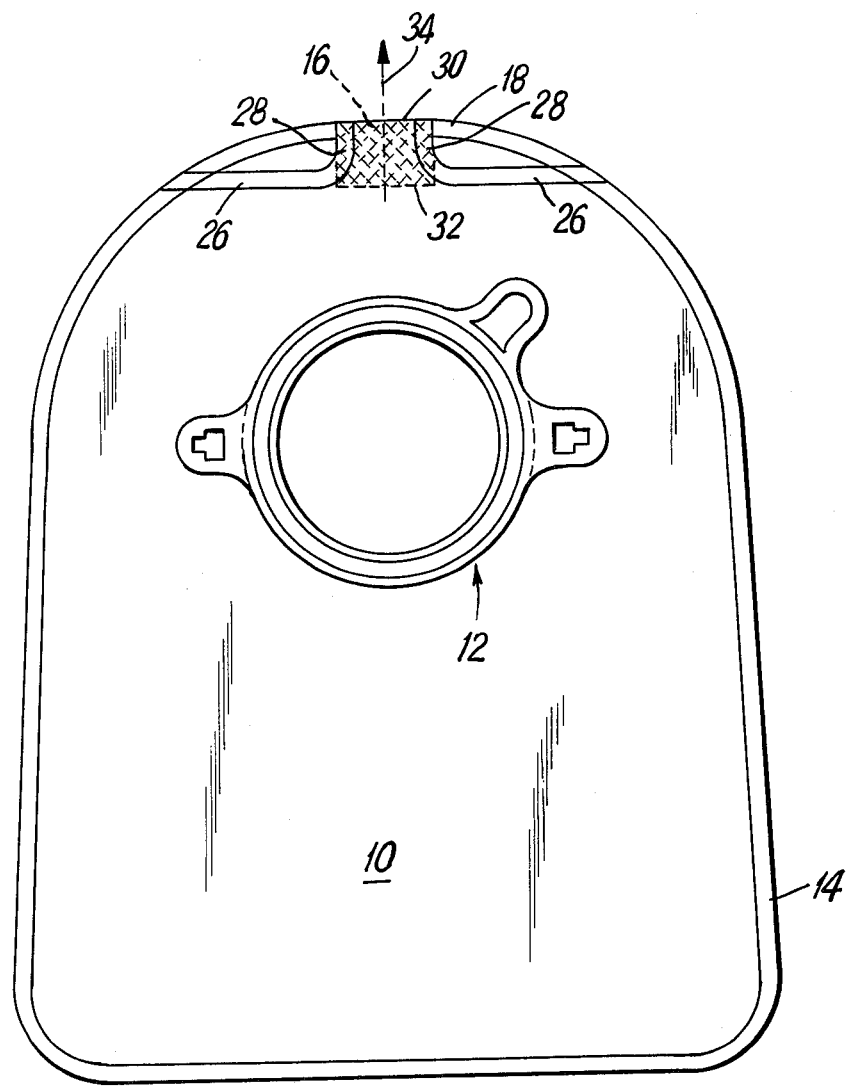
FIG. 1 is a front view seen from the position of the wearer of our example of ostomy bag according to the invention.

The ostomy bag illustrated in FIG. 1 has front and rear walls of which the rear wall is shown at 10. In this specification, "front" and "rear" are used in the sense that the front wall of the bag is the wall further from the wearer when the bag is being worn. The rear wall has a central circular orifice to which is applied one coupling member of a coupling for securing the bag to the user. An advantageous design of coupling is disclosed in U.S. Ser. No. 881,274 filed on Feb. 27, 1978. The body-side coupling member is shown at 12. The two walls of the bag, preferably of a synthetic plastics material (that known as SARAN is suitable) are welded together (usually heat-welded) by a weld 14 around their periphery. The welding tool used is such as to provide a special configuration of weld seams in the top region of the bag. A substantially rectangular piece of activated carbon cloth 16 is placed between the walls of the bag, centrally at the top edge of the bag, and the weld seams at that region provide a peripheral weld 18 and two welds and each of which has a generally horizontal portion 26 and a generally vertical portion 28 which at its top end merges with the weld 18. The portions 28 overlap the carbon cloth and secure it firmly in position. The region 30 at the periphery and the region 32 between the bar weld portions 26 are left unwelded, that is, the welding electrode or bar is interrupted at those regions. Hence there is a gas path edgewise through the carbon cloth 16 to the exterior of the bag as indicated by the arrow 34. The boundaries of this gas path are formed by the front and rear bag walls and the two weld portions 28.

The activated carbon cloth element 16 is preferably prepared according to the disclosure in British Pat. No. 1,301,101.

Figure 2:
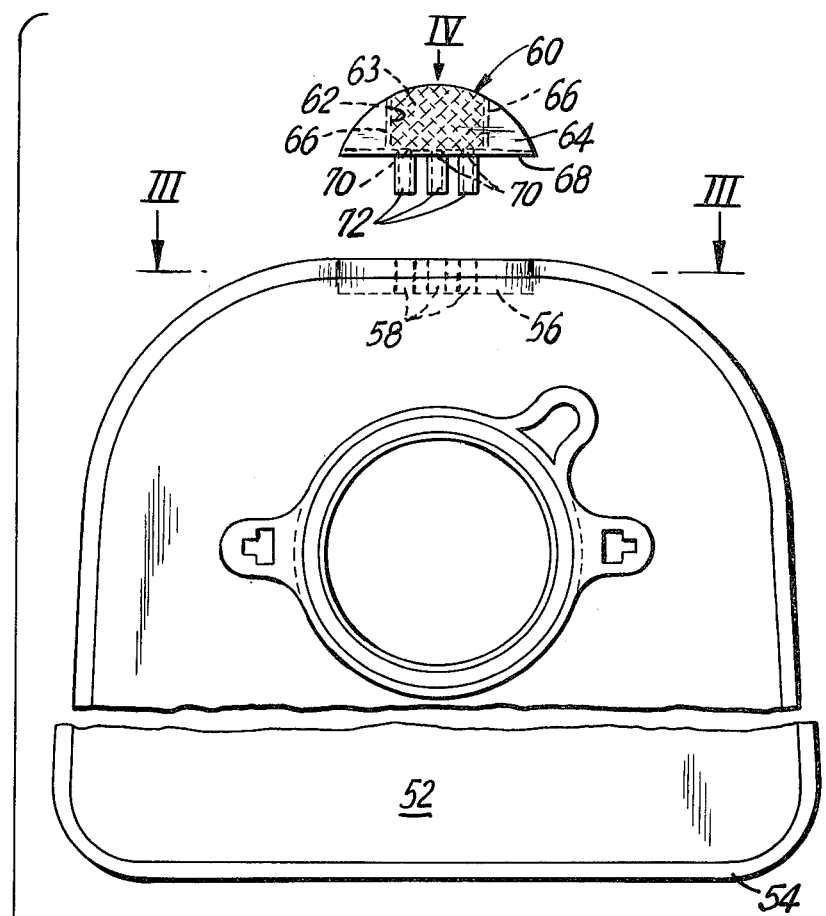
FIG. 2 is a similar front view of a second example of ostomy bag according to the invention.
Figure 3:
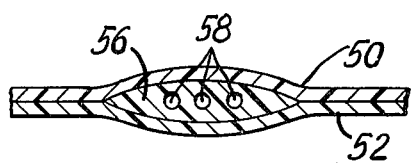
FIG. 3 is a cross-section on the line III—III in FIG. 2.
Figure 4:
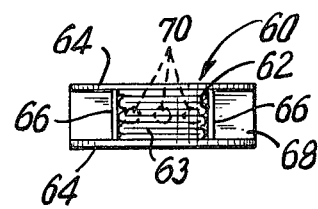
FIG. 4 is a top view of the cartridge looking in the direction of the arrow IV in FIG. 2.

A second example of the invention is illustrated in FIGS. 2 to 4. The ostomy bag has a front wall 50 and a rear wall 52 connected by a peripheral weld 54. Disposed between these walls and welded to both is an insert block 56 having three holes 58 therethrough extending from the interior of the bag to the exterior. The axes of the holes 58 are parallel to each-other. The block is preferably but not necessarily of synthetic plastics material. The purpose of the block is to provide a mounting and an attachment point for a filter cartridge 60. This may be of moulded plastics material and has a filter-receiving compartment 62 defined by front and rear walls 64 and side walls 66. The bottom wall 68 of the cartridge has three holes 70 therethrough and extending from the bottom wall are three hollow pins 72. These pins are a snug push fit in the holes 58 in the block. That is to say, the cartridge 60 can readily be inserted and removed by pushing the hollow pins 72 into the holes 58, and, once inserted, is reliably maintained in the top edge of the bag by the snug fit between the pins and the holes. The compartment 62 contains filter material. This is preferably folded woven activated carbon cloth 63.

Again, the carbon cloth 63 is preferably prepared as disclosed in British Pat. No. 1,301,101. As can best be seen in FIG. 4, the cloth material is preferably folded in layers with the planes of the layers parallel to those of the walls 64. It will be seen that there is thus defined a gas path for escaping odorous gases through the hollow pins, through the filter material in the compartment 62 and out of the top of the cartridge. In this way, the gases are largely or wholly deodorized. As an optional refinement, a masking perfume may also be contained in the cartridge.

In another embodiment of the invention, a flat hollow housing is welded into an upper edge of the bag so that it is sandwiched between the front and rear walls, and the interior of the housing is provided with a filter material. In such an arrangement, the flat hollow housing may contain a bobbin having a central mandrel upon which activated carbon cloth is wound, the flanges of the bobbin being substantially gastight fit with the housing and being provided with apertures positioned so that gases passing therethrough are constrained to pass mainly through the carbon cloth wound on the mandrel.

In yet another embodiment of the invention, the hollow housing may contain activated carbon granules. The housing may be a thin rectangle block of synthetic plastics material seen in section perpendicular to the gas path therethrough, the bag walls being welded to the long sides of the rectangular housing.

In a further modification of the invention, the filter is provided by a thin plug of suitable porous foam plastics material which is located between two layers of woven carbon filter cloth. The filter is again located in a position which will be on the top of the bag when it is in use and the filter cloth is wrapped around the bottom and each side of the plug. The wrapped plug is then welded into the bag edge, the direct weld between the two sheets which defines the outline of the bag being interrupted at this point and at this area the two sheets forming the bag being welded to the foam plastics plug.

What is claimed is:

1. An ostomy bag formed by a front wall and a rear wall both of plastics material welded together around their periphery except at a portion of one edge which is at the top of the bag when it is in normal use, filtering means comprising a flat hollow housing the interior of which is provided with filtering material, said housing is formed from synthetic plastics material and is a thin substantially rectangular block whose long sides intersect at both ends of said block to form tapers when said block is viewed in section parallel to the gas path therethrough, said housing having a plurality of holes therethrough leading from the interior to the exterior of said bag, said bag walls being welded to the long sides of said housing so as to form a gas tight seal at the top edge of said bag, and said rear bag wall having an opening adapted to receive the stoma of the user.

2. A bag according to claim 1 in which said filtering material is activated carbon cloth.

3. A bag according to claim 1 including on said rear wall around the stoma opening means to attach the bag directly or indirectly to the body of the user.

4. An ostomy bag formed by a front wall and a rear wall both of plastics material welded together around their periphery except at a portion of one edge which is at the top of the bag when it is in normal use, an insert block of synthetic plastics material, said bag walls welded to the outer periphery of said insert to form a gas tight seal at the top edge of said bag, said insert having a plurality of holes therethrough leading from the interior to the exterior of said bag, and a filter cartridge having a series of hollow pins dimensioned to fit snugly in said holes and a filter-receiving compartment containing filtering material, the arrangement being such that gas passing from the interior to the exterior of said bag passes through said hollow pins, into and through the filtering material in said cartridge, and out of an escape vent from said cartridge.

5. A bag according to claim 4 in which said cartridge filter material is activated carbon cloth.

6. A bag according to claim 4 including on said rear wall around the stoma opening means to attach the bag directly or indirectly to the body of the user.

* * * * *